(12) United States Patent
Chinaglia et al.

(10) Patent No.: US 7,967,438 B2
(45) Date of Patent: Jun. 28, 2011

(54) SYSTEM FOR OBTAINING A FUNDUS IMAGE

(75) Inventors: Djalma Antonio Chinaglia, São Carlos São Paulo (BR); Mário Antonio Stefani, São Carlos São Paulo (BR); Érica Gabriela De Carvalho, São Carlos São Paulo (BR); Jarbas Caiado de Castro Neto, São Carlos São Paulo (BR); Daniel Dos Santos Júnior, São Carlos São Paulo (BR); Rodrigo Gonzalez Modugno, São Carlos São Paulo (BR)

(73) Assignee: Opto Electronica S/A, Sao Carlos SP (BR)

( * ) Notice: Subject to any disclaimer, the term of this patent is extended or adjusted under 35 U.S.C. 154(b) by 0 days.

(21) Appl. No.: 12/292,742

(22) Filed: Nov. 25, 2008

(65) Prior Publication Data
US 2009/0128775 A1    May 21, 2009

Related U.S. Application Data

(63) Continuation of application No. 11/450,867, filed on Jun. 12, 2006, now Pat. No. 7,470,024.

(51) Int. Cl.
*A61B 3/14* (2006.01)
*A61B 3/02* (2006.01)
(52) U.S. Cl. .................. 351/206; 351/209; 351/232
(58) Field of Classification Search .......... 351/206, 351/208, 209, 222, 232, 233
See application file for complete search history.

(56) References Cited

U.S. PATENT DOCUMENTS

| 5,537,162 | A | 7/1996 | Hellmuth et al. |
|---|---|---|---|
| 7,048,379 | B2 | 5/2006 | Miller et al. |
| 7,364,296 | B2 | 4/2008 | Miller et al. |
| 7,470,024 | B2 * | 12/2008 | Chinaglia et al. ............. 351/206 |
| 2005/0041207 | A1 | 2/2005 | Miller et al. |
| 2006/0058682 | A1 | 3/2006 | Miller et al. |
| 2006/0187462 | A1 | 8/2006 | Srinivasan et al. |
| 2006/0268231 | A1 | 11/2006 | Gil et al. |
| 2007/0159600 | A1 | 7/2007 | Gil et al. |

* cited by examiner

*Primary Examiner* — Jessica T Stultz
*Assistant Examiner* — Brandi N Thomas
(74) *Attorney, Agent, or Firm* — The Nath Law Group; Jerald L. Meyer; Derek Richmond

(57) ABSTRACT

The present invention is related to a system for obtaining a fundus image, constituted by optical means implemented in an equipment to observe and photograph the image of the wall fundus (16), comprising a capturing optical means composed by high sensibility digital camera, constituted by an image sensor (2) and focal optical system (3), said digital camera being used to register a captured image by an afocal optical system, composed by a capturing lens (13) and its afocal complement (6); a lighting optical means provided from a arrangement conformed with optical fiber bundle (7), (8), (9) and (10), halogen light source (23) or light emitting diode source (LED); wherein said light beam from the halogen light (23) or light emitting diodes has an annular form when it pass in the anterior part of eyeball (14) and focus in the pupil plan (15); both the means having the optical path partially common over the optical axle (1) from the optical fibers arrangement (7), (8), (9) and (10) to the fundus (16), region in that both the beams are coaxial; in that both the optical means are equipped with light polarizers (4) and (11), being integrated with mechanical, electronics and computerized components, and applicative program, which allow control the equipment and its multiple operational configurations, conducing image acquisition and processing, and displaying the results.

8 Claims, 4 Drawing Sheets

SYSTEM FOR OBTAINING A FUNDUS IMAGE

FIELD OF THE INVENTION

Figure 1:
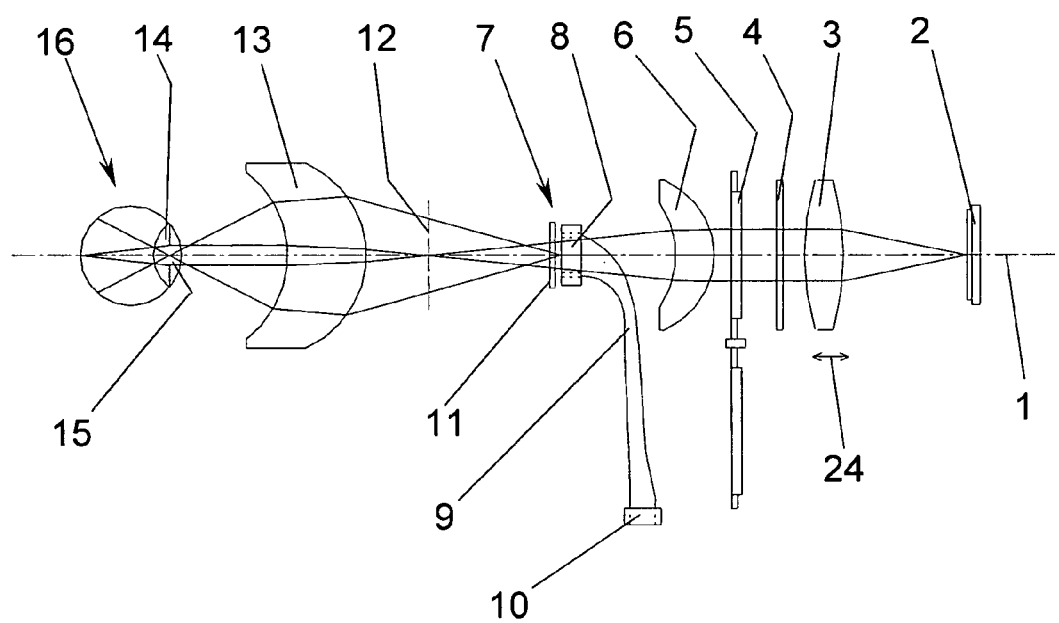

The present invention refers to a system associated to a device applicable in opthalmology, developed to obtain an image of the retina and to carry out diagnosis of the fundus.

BACKGROUND TECHNIQUE

Conventional equipments projected to obtain fundus images are mainly based on a technique widely known and used in opthalmology, which predicts the wide and uniform lighting of the fundus wall, followed by frontal capture of the reflected light in this process. The light beam used for lighting should according to this technique, penetrate in the back portion of the eyeball through its periphery c region, allowing that the region near to the optical axis be free of intense lighting, in order to not contaminate with spurious lighting the reflected beam that returns bringing the image of the fundus.

In order to achieve these objectives, it was adopted for the lighting beam, as more appropriate an annular form, since it has a cylindrical symmetry, so, allowing distribute the light beam on the whole circle of the pupil periphery. This annular beam must have its focal position adjusted in the iris region, which coincides with the pupil plan, and shows in this plan a diameter slightly less than the pupillary opening. However, said beam must also have a elevated divergence from its focal position, to reach the fundus with a wide and uniform energy distribution.

The lighting beam should have necessarily an elevated intensity, so that a significant quantity of scattered light by the fundus returns through the pupillary opening, and be sufficient to sensitive the used camera. This is necessary because the fundus wall has the characteristics of a diffuse irradiator, working better as a scatter surface as a light-reflecting surface. The light reflectivity is a function of the surface properties, the incidence angle, and light wavelength, being more accented in higher wavelengths, near to the red visible limit. So, the fundus wall has a low inherent reflectivity.

This necessary elevated intensity is another good reason that the lighting beam presents a ring form, because the excessive spatial concentration of the lighting beam energy would affect in a adverse form the intraocular medium, which it is formed by the cornea, anterior chamber, iris, lens and pupillary opening. The annular form provides a regular distribution of light energy on the whole extension of the peripheral line of the frontal part of the eye, even that it is considered that the line of light ring has a narrow width in its focal position. This method also allows a more uniform lighting of fundus by the cylindrical symmetry that the ring form provides. The geometry of the construction and the depth of focus should be adjusted in order to obtain the most wide and uniform possible lighting.

The simultaneous capturing of the scattered light by the fundus portions undergone to this lighting is carried out, still according with this technique, with an optical system and a device to register the image. In some old equipment models the lighting beam has not the ring form, but a simple beam form that reaches the eye in the pupil periphery and projects the light straightly in a small region of the fundus. This beam has a small angle in relation to the eye optical axis, whereas the capturing is generally frontal. In these equipment models the inspection of fundus is carried out by regions, which increases the examination difficulty and increases the risk for the patient due to excessive intensity of a punctual beam.

The anterior part of the eye and the intraocular medium have differentiated structures, in whose interfaces occurs an accented scattering of incident light, this is the principal reason for which the lighting must pass this region by its periphery and in a beam form as narrow as possible, to avoid possible scattering in these structures may contribute with undesirable light stains in the image fundus. The appearance of reflexes from the peripheral region is reduced because the annular beam reaches the cornea in a remote point of the optical axis, in which the incidence angle away from the normal to the surface makes that the principal reflection be launched far from of the optical axis, and out of the capturing lens.

The means must have a part of its optical paths in common, due to an inevitable spatial superposition of both beams in the intraocular medium and in the region immediately in front of the eye, causing that the capturing lens should capture the light coming from the fundus and focalize the lighting beam in the pupil plane. The most used solution in order to combine said optical means, is to put between the capturing lens and the others means components, an oblique mirror having a central hole, which function is allow the partial sharing of the optical axis by both optical means, so that the capturing beam passes by the central hole of the mirror and propagates backwards, while the lighting beam fall on obliquely on the mirror being reflected from that to the eye.

The mirror position is calculated in order to be in the focus of a primary and real image of the light ring projected by a first optical set of the lighting means, and also be conjugated to the iris position by the capturing lens. The image formed in the mirror by the first optical set is generally produced by placing two screens shutters in the same plan, one circular and other with a circular hole, whose diameter is a bit higher than the first one. The first optical set of the lighting means must be used to focus the ring in a position near to the mirror plan.

As the lighting should be intense and sufficient to that the reflected light by the fundus be above of the threshold sensibility of the image sensor, and as the intensity of the return beam is less than the intensity of the lighting beam, it is essential remove the reflections of the most intense beam. The principal reflections take place in the cornea, in the eye internal interfaces and in the lenses used in common by the two optical means, because the reflected light may contaminate the capturing beam, causing stains and brighten points in the image, besides elevating the bottom intensity level of the image.

The basic proceeding adopted to remove the reflections in this model, is the use of polarizers placed in the lighting and capturing means, in that the polarizer of the capturing means is orientated perpendicularly to that placed in the lighting means, that is, the fundus is illuminated by polarized light and the capturing means receives light only with crossed polarization. The polarizer of the lighting means is constituted of an object with an annular form, with dimensions slight bigger than the thickness of the ring light, and placed in front of the outlet end of the optical fibers arrangement.

The technique is based on a physical principle that establishes the properties of light interaction with the material means, and defines the effects on the light in accordance with the characteristics of the material. The materials which surface is polished, or smooth, reflect light with higher efficiency, because the most part of the bright energy is reflected by an angle equal to the incidence angle, in a so called situation of speculate reflection, while materials with rough, or wrinkled surface, reflect light in a diffuse way, scattering the incident radiation in a wide angular band. These phenomena have consequences on the polarization of incident light, so that the speculate surfaces reflect light with polarization almost equal to the incident light, at least for angles near to normal, while the diffuse surfaces not polarizes the incident radiation, reflecting light with random polarization.

This physical process establishes a criterion to distinguish the light originating from the fundus from that originated by reflections coming from speculate surfaces of the eye and from the optical means, since the crossed polarizer of the capturing means blocks all light with parallel polarization to the lighting beam, allowing that only the light with perpendicular, or orthogonal polarization, to the lighting beam, passes. The capturing beam has a considerable fraction of light that passes by the polarizer, since its polarization has a random distribution, and so, always has a parallel component to the polarizer direction. To reach efficiency the system must be optimized so that the light beams pass the most lenses surfaces in angles near to a normal of the surface, so that the polarization phenomenon by reflection does not affect the system, since this phenomenon is characteristic of angles near to Brewster.

There are varied light source used in the construction of lightning means, such as incandescent lamps and halogens, which have a wide spectral band and relatively high intensity in wavelengths in the visible band, from infrared and of ultraviolet. Tungsten incandescent lamps are more stable and have more simple operation, while the halogen lamps support better a continuous operation regime. The spectral curve of halogen lamps is shifted for shorter wavelengths in relation to incandescent lamps, presenting a reasonable intensity in the ultraviolet band, although this curve vary during the use, its intensity remains quite stable. The fluorescent light, as the high-pressure xenon, also having a wide spectral band are used in more complex and expensive equipments. All these lamps present common difficulties, as the excessive divergence of irradiated light that makes necessarily the use of diaphragms, the low energetic efficiency accompanied by high heat dissipation, and the compulsory placing of filters to cut undesirable wavelengths in determined examinations. The divergence makes difficult the beam collimation and the efficiency in the capturing of emitted energy, producing not uniform lighting in the fundus if the optical means is not well corrected. The necessity of illuminating a wide region in the fundus demands a light source with a relatively big emission surface, positioned in the focal point of the lighting means, due to placing of screens shutters, also big, with the ring form.

The light emitting diodes (LED) and laser diodes also can be used alternatively as light source, since they present less divergence in the light emission. But the predominant necessity of wide spectral band and elevated intensity makes difficult the option for these components. The use of light emitting diodes (LED) is extremely advantageous as a low cost option for multiple images acquisition, using the light pulses (flashes) synchronized to the acquisitions, because the others light sources demands an excessive wait time for the electronic reload.

SUMMARY OF THE INVENTION

With the objective in overcome the above-described drawbacks, its is provided, according to the present invention, a system to obtain a fundus image constituted basically by two different optical means, called lighting means and capturing means, which has coaxial optical paths and partially superimposed.

The lighting means has the function in projects in the fundus a light beam that will be scattered in all directions by the structures of the fundus wall. While, the capturing means has the function in registers the retina image and other structures of the fundus wall, capturing a reflected light portion that emerges from the pupillary opening. The two mainly optical means which compose this equipment are supported by structures and mechanical devices, fixed and adjustable, and by electric and electronic circuits, servomechanisms, computer and software, which are used for controlling the equipment, data acquisition, images processing and displaying the results.

Said lighting means projects a light beam which cross section has a fine ring form of light in the pupil passage, but presents divergence from this point, reaching fundus with a uniform distribution of energy. This light ring must pass the pupil plan with a diameter slightly less than the pupillary opening, so that the circle of the ring is adjusted in said opening with the ring line going through its periphery. The ring focal position coincides with the pupil plan making the circular line of the ring as narrow as possible in this plan.

The capturing means includes an optical set as a Kleperian astronomical telescope shaped in the situation of conjugated infinite, characterizing an afocal optical system. This mean is made by a set of capturing lenses placed immediately in front of the eye to be examined, and a set of lenses that work like its afocal complement. The afocal optical system transmits the fundus image to a high sensibility digital camera made with a focal lens in front of an image sensor, in which the optical elements of the focal lens are placed in a mechanical adjustable device, which allows optimizing the image focus exactly on the image sensor. Considering that the eye optical elements itself contribute to the capturing means, the composition of the afocal system with the eye, works exactly like an altered system of an astronomical telescope associated to the eye of the observer, with the difference that in this case the fundus is not the receiver of the image, but the object to be observed.

The lighting and capturing optical means follows to known principles in opthalmology, which establishes that there must be a partial superposition of lighting and capturing beams, since the optical elements of the eye contribute to both means. Besides, in order to obtain a uniform lighting of the fundus and a frontal capturing of the returned image, it is convenient that the optical axis coincide and the capturing lens be used like a common element to the two main optical means of equipment. All these requisites lead to geometry with cylindrical symmetry for the system set.

Said lighting means also presents a common architecture in the equipments existing in the market. However, it includes an innovation developed for the present invention, the use of a specific optical fibers geometrical arrangement simplifying its construction and alignment. Said optical fibers arrangement has excellent coupling to the light source in one end of the fibers, a light emitting object with a ring form in another end and an opening for passage of capturing beam by the center of this ring.

The spurious reflections presents in the image are removed using light polarizers, used in the two means. The polarizers placed in the capturing and lighting means are disposed orthogonal, that is, the polarizers have crossed directions. This arrangement of the polarizers reduces with great efficiency the light originating from reflections in the lenses of the optical system and in the interfaces of the eye itself, like the cornea, and represents another innovation in this invention.

The appliance set is supported in a mechanical device suited in a table with adjustable height, in order that the equipment can be positioned in the best situation for examination, there is a support and fixation structure for the patient head, which allows a quick placing of the eye in examination through a gauntlet that makes possible the movement of the equipment set in the horizontal plan and in the vertical direction, besides rotation on the axis that passes vertically by the center of the eye. The optical axis of lighting and capturing beam must be near to the optical axis of the eye during the examination.

The optical, mechanics, electronic, and computational resources, besides the applicable program incorporated to the equipment set allow its configuration in four operational ways and the realization of four different types of opthalmologic examinations. Through the selection of optical filters, with specific passages bands, that can be inserted in the optical paths of lighting and capturing means, it is possible to enable the equipment for differentiated examinations, with the optical system that allows a complete mapping of fundus with good quality images, besides be quickly, easiness and operational comfort.

The device herein proposed, on the contrary of the conventional models, uses a projector made with an optical fibers bundle molded in a single piece, which it is placed between the light source and the capturing lens in substitution of the holed mirror, which is expendable in this model, since that the optical fibers outlet is adapted in the ring form. Besides the mirror, the set of lenses for the formation of the primary image also becomes expendable, since the optical fibers outlet itself is the object to have its image projected. This formed piece substitutes with advantage the optical systems and screens shutters generally used in order to project the ring. The other end of this fibers optical bundle is molded in a terminal with excellent coupling on the light source, which increases considerably the efficiency in inserting the light in the fiber, and the use of the bright energy of the lamp using a simple parabolic mirror system and lenses that focus the light emitted by the halogen lamp to the inlet end of an intermediary optical fiber, which drives the light from the source to the optical fibers arrangement.

The advantage of this system is that the new light emitting object, the optical fibers ring, has light points with reduced dimensions, small divergence and Gaussian angular distribution in the beam intensity, allowing the reduction in the size of the projector, and makes the collimation and beam focusing more simple, besides provide a more fine beam and with great brightness. The line of light obtained is much more fine, avoiding the use of circular diaphragms in the system, and the presence of a oblique branch of lighting beam. The simplicity achieved with this arrangement practically removes any difficulty in the optical alignment of the system making the equipment compact, reduced, light and with great impact resistance.

The system emits light in a safe power level and appropriate to each used wavelength, and with spectral band defined for each type of examination, selected through insertion of the respective sets of filters in the optical paths of each mean. These instruments are configured to carry out up to four types of different opthalmologic examinations, and are destined to obtain basically images, which after processed allow to determine the characteristics of the retina, its blood vessels and many others details of fundus.

The system for obtaining a fundus image, object of the present invention, accomplishes to the requisites and concepts presented previously, and add innovations that make easy its implementation and perfect its performance.

DETAILED DESCRIPTION OF THE DRAWINGS

Figure 2:
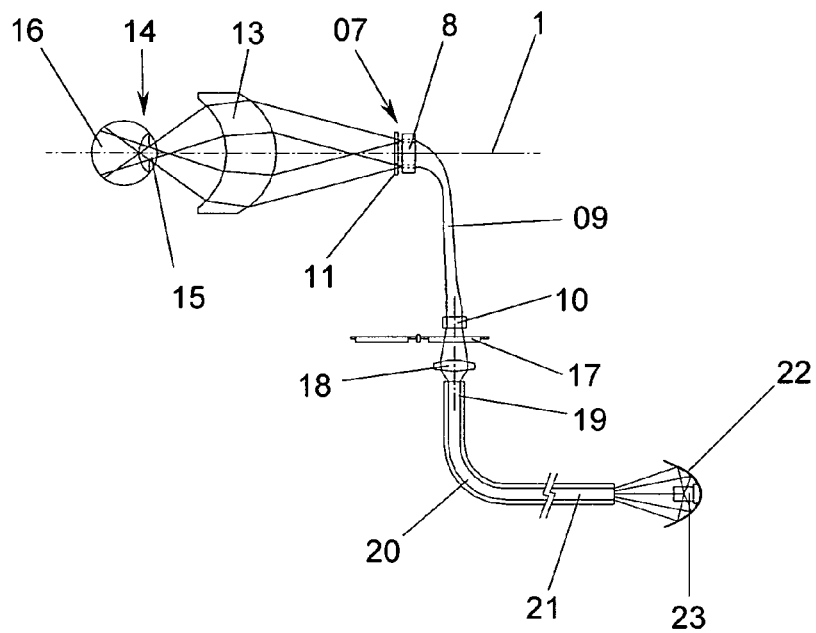
Figure 3:
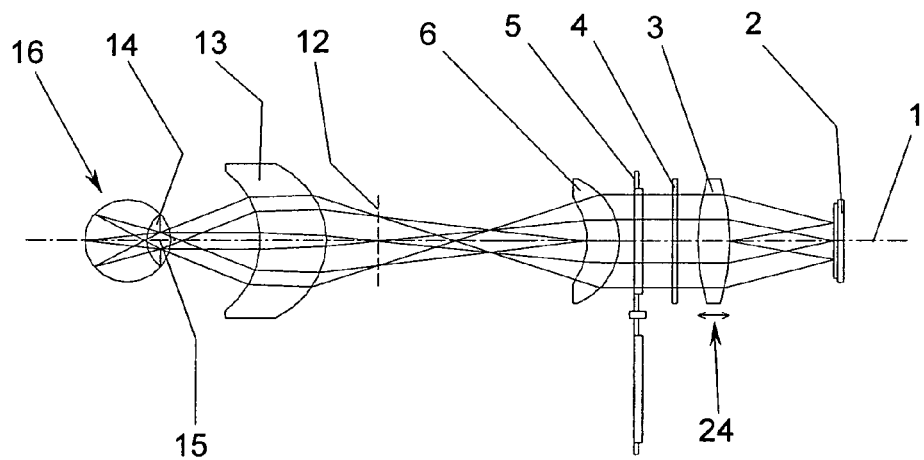
Figure 4:
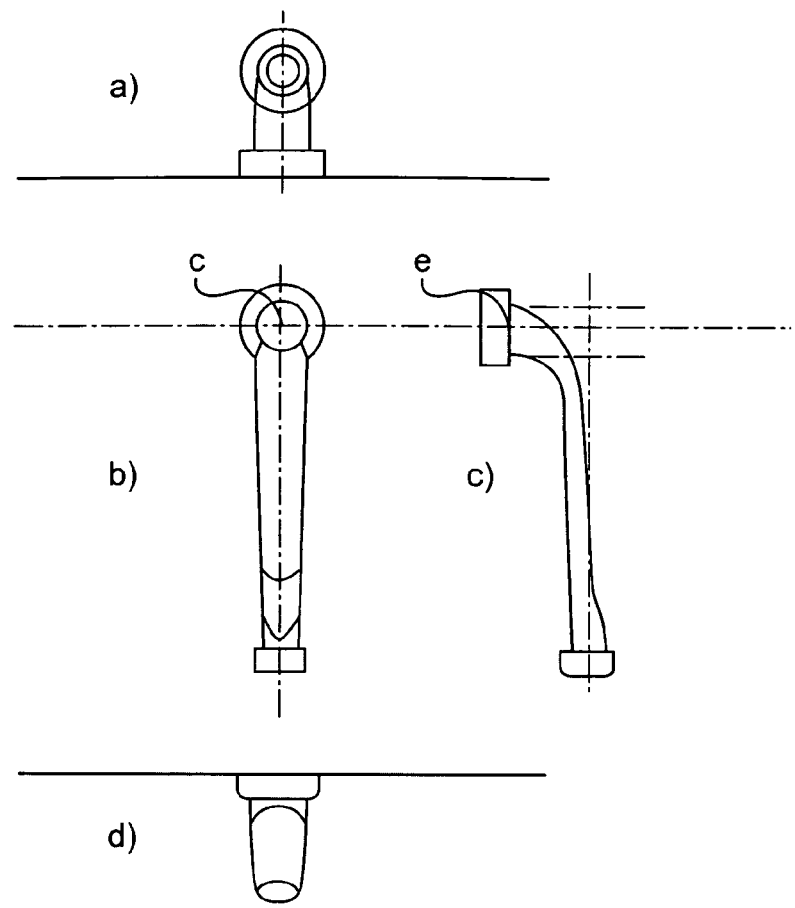
Figure 5:
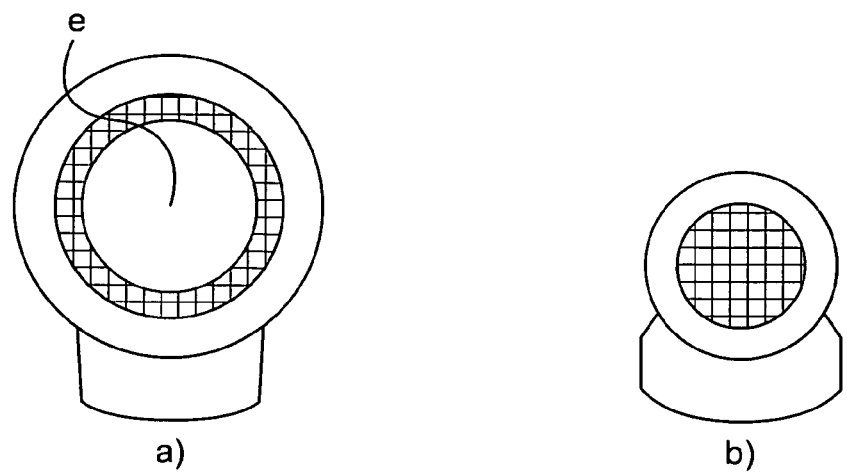
Figure 6:
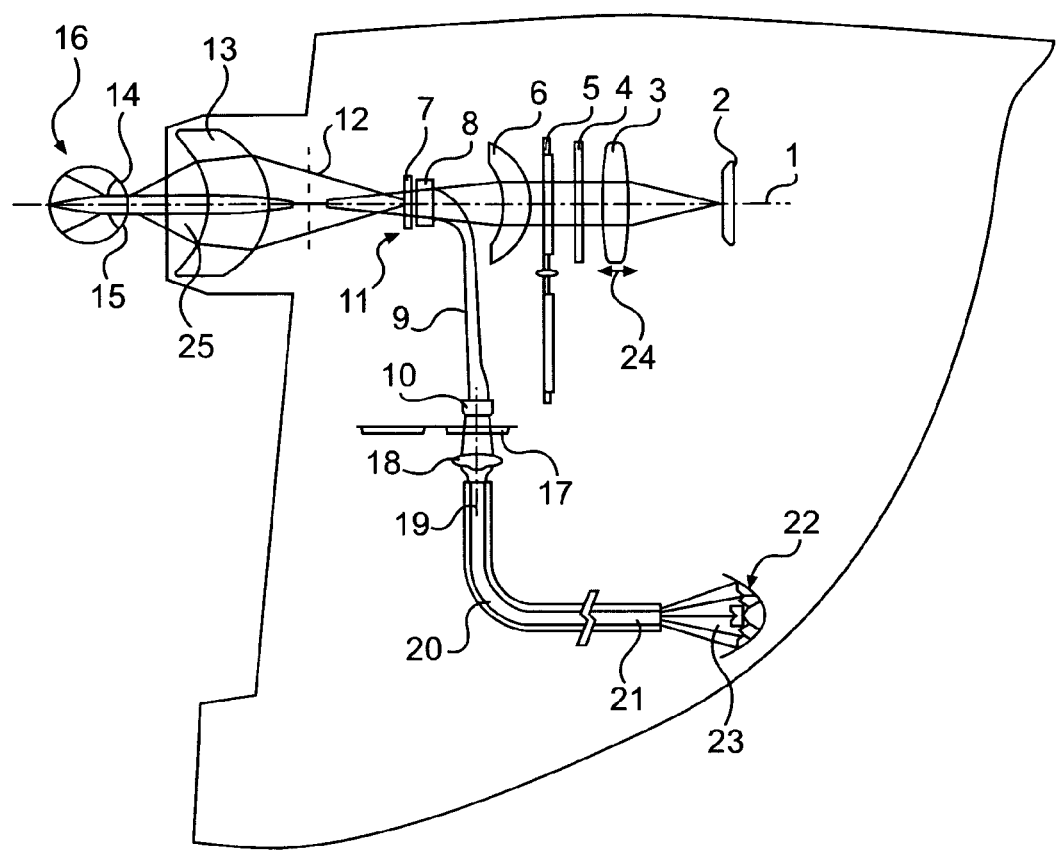

Other objectives, characteristics and advantages of the system for obtaining an fundus image, subject of present invention, will be more apparent from the detailed description, according the drawings as follows:

FIG. 1—is a schematic representation of the technique presenting the basic principles used in the construction of the system;

FIG. 2—Shows a detailed lateral view of lighting means and of the eye in examination;

FIG. 3—Shows a detailed lateral view of capturing mean and of the eye in examination;

FIG. 4—Shows details the arrangement in ring form built with optical fibers;

FIG. 5—Shows details of the ends of optical fibers arrangement, where occurs the coupling to the light source and the emission of the beam in a ring form; and FIG. 6—Shows a lateral view of the system, showing the fixed base, the adjustable tower, the support base of the chin, the table and the gauntlet that allow the adjust of the patient eye.

DETAILED DESCRIPTION OF INVENTION

As showed by figures, where identical numeric references identifying equivalents parts, the system for obtaining a fundus image, object of present invention is constituted basically by two different optical means, which are typical of a retinograph, and called lighting means and capturing means. These means are described separately and present optical coaxial paths 1, with the superposition in a passage of its distances between the fundus 16 and the arrangement outlet end of the optical fibers 7. The optical means are implemented in a equipment that has mechanical structures, fixed and adjustable, to support the components, besides electronic circuits, computer and applicable program, used for control the equipment, images acquisition, image processing and displaying the results.

The first optical mean has the function to illuminate the fundus with a light beam that, must present two essential characteristics, whereas the first characteristic is to pass the frontal part of the eye by its peripheral region, while the second characteristic is to reach the fundus with a uniform distribution of energy. The requisite that the beam trajectory is contained exclusively in the peripheral region of the frontal part of the eye has the objective in avoid the reflection and light scattering in the intraocular medium, leaving the pupil central region free of intense lighting.

The second optical means has function in capturing the image produced in the lighting process being constituted by two lenses sets and a high sensibility digital camera. These lenses sets form a system characterized like an altered afocal telescope, in that the first set is called of capturing lens, or eyepiece, and the second set is constituted by its lens, working like the afocal complement of the capturing lens.

The FIG. 1 shows the used technique showing a complete scheme of the two main optical means, and its basic working principles, whereas the elements 7, 8, 9, 10, 11 and 13 correspond to the optical components of the principal part of the lighting means, and its optical axis 1. The elements 14, 15 and 16 represent the eye being deeply illuminated; with the beam reaching the fundus wall 16, after passes by the frontal part of the eye 14, which includes the cornea, anterior camera, iris, lens and pupillary opening 15. The complete capturing means includes the elements 2, 3, 4, 5, 6, 8 and 13 herein represented by the digital camera 2, 3; and by capturing lens, or eyepiece of the mean 13, its afocal complement, or means lens 6, optical set of filters 5 and light polarizer 4, which proceed the image acquisition formed by the light reflected on the fundus 16. The camera is constituted by a focal lens 3, which registers the image formed on a CCD image sensor type 2. The optical axis 1 common in both optical means must be adjusted during the measure proceeding in order to approximately coincide with the optical axis of the eye in examination 14, 15, and 16. Also in the FIG. 1 there are the distances that define the plans of the pupil 15 and the arrangement outlet end of the optical fibers 7 as conjugated distances by actuation of the capturing lens 13, when considered as an integrant element of the lighting means. However, when considered as an integrant element of the capturing means, the capturing lens 13 collects the light that goes out from the pupil 15 and a fundus primary real image 12 is formed between this capturing lens 13 and the passage orifice 8 of the capturing beam, in a position 12 that can present a small variation depending on the patient eye diopter 14, 15, 16. Said primary real image 12, is focused on the image sensor 2, by the afocal system lens 6 together with camera focal lens 3, after the capturing beam passes the orifice 8 of the optical fibers arrangement 7, 8, 9, 10. It should be observed that the eye optical element 14 acts together with the capturing lens 13 in the formation of the primary real image 12.

In the FIG. 2 it is shown in details, the complete lighting means in a lateral view, whereas the used technique in this means is shown up, in that an annular light beam is produced to penetrate the eyeball 14, 15, 16 through the periphery of the eye anterior part 14 and illuminates uniformly the whole extension of the fundus 16.

The called optical fibers arrangement is obtained from a piece 7, 8, 9, 10 made with a bundle of optical fibers 9 shaped in a curved geometrical form and lengthened, been like a pipe, which ends 7 and 10 are fixed by steel rings, in order to obtain the coupling of the light source at the end 10, a light emitting object with ring form at the end 7 and an opening 8 for the passage of the capturing beam by the centre of this ring. The annular beam is projected from the fibers outlet end 7 passing the light polarizer 11, also in a ring form, in order to not obstructing the orifice 8, whereas the capturing beam passes.

The light source used in this specific projector is a halogen lamp 23 coupled to the entry end 21 of an intermediary optical fibers bundle 19, 20, 21 associated to a concave mirror 22, which has the function in focusing the maximum possible amount of light emitted by the lamp in the entry of the fibers bundle, considering the diameter of these fibers and its numerical opening.

The intermediary optical fibers bundle 19, 20, 21, has the outlet end 19 coupled to a entry end of the optical fibers arrangement 10, with the set of condensing lenses 18, whose function is focuses the light emitted by the intermediary bundle in the entry of fibers arrangement by coupling its respective numerical openings and diameters. Said halogen source 23, emits light in a wide specter of wavelengths, including the ultraviolet band, all near the visible and near infrared, optical filters are used to blockade the ultraviolet band.

The intermediary couplings between the halogen lamp 23 and the entry end 10 of optical fibers arrangement 9 were designed in order to maximize the light entry in the said optical fibers 9 and homogenize the distribution of light along the line of the ring formed in the optical fibers outlet end 7. The optical filters set 17 of the lighting means is positioned immediately before the optical fibers arrangement 7, 8, 9, and 10. It is possible through mechanical adjusts set the focal distances and placing the couplings ends between the optical fibers bundles 9, 20, in order to allow the maximum insertion of energy in the fibers.

Alternatively, it can be used as a light source, a set of light emitting diodes (LED) covering a wide band, which would allow the midriatic use, in that the fundus is illuminated by a set of infrared LED's. In order to obtain a colorful fundus image or "Red Free", with visible radiation, the LED is blinked quickly, offering more comfort to a patient.

Said means projects an annular light beam relatively intense, when compared with the quantity of light that returns reflected by the fundus 16, in the same optical path 1, which represents a small fraction of the intensity of the lighting beam. The beam has the form of an extremely fine ring in its passage by the pupil 15, with a diameter slightly less than the pupillary opening and approximately concentric to the optical axis of the eye. As observed in the FIG. 2, in a lateral view, this light beam been emitted peripherical in the outlet end 7 of the optical fibers arrangement, reaching the capturing lens 13, being focused in the circle that defines the periphery of the pupil 15, and diverging from that, in order to illuminating uniformly the fundus 16.

The FIG. 3 shows in details a lateral view of the complete capturing means formed by elements 2, 3, 4, 5, 6 and 13, that should capture and register a good quality image of fundus 16.

The capturing lens 13 is placed against the eye in examination 14, 15, 16, and should receive the whole light that passes by the pupillary opening 15 bringing back from the fundus 16, subtended by an angle less than 22.5° of semi-opening, while the afocal lens 6, projects in front the afocal beam produced. The capturing lens 13 must be positioned quite near and in front of the eye 14, 15, 16, so it is necessary that said capturing lens 13, be a common component to the two optical means, and that combines the two beams in a unique optical path whose axis 1 coinciding. The most appropriate construction to become the beams be coaxial, is that the capturing beam passes by the ring orifice 8 formed by the optical fibers arrangement 7, 8, 9, 10 proposed in this technique. The functional project of the capturing lens 13 and of central orifice 8 of the optical fibers arrangement must be satisfactory to the requisites of these two means simultaneously. The digital camera 2, 3 that also composes the capturing means is constituted by a set of lenses that form the camera focal lens 3, which project the fundus image 16 on a sensor 2 made with a matrix of photosensitive elements. In the capturing means, the set of optical filters 5 and the light polarizer 4 are strategically positioned between the afocal system 6 and 13 and the camera focal lens 3, because in this region the rays of the capturing beam are parallel having just surfaced the afocal system.

The focusing lens set 3 of the image, placed in front of the image sensor 2, as well as the lens 6 of the afocal system, do not interfere in the performance of the lighting means since they are not in the same optical path.

The system magnification is maintained fixed by the self-characteristics of the afocal system 6, 13, whose lenses are maintained rigidly in its positions, in that important bonds of the system are not altered. However, the focuses adjust in the focal lens of camera 3 produces a small alteration in the magnification.

The FIG. 4a shows an inferior view of the optical fibers geometrical arrangement 7, 8, 9, 10.

The FIG. 4b shows a frontal view of the optical fibers geometrical arrangement 7, 8, 9, 10 and an opening e in the optical fibers bundle, The FIG. 4c shows a lateral view of the optical fibers geometrical arrangement 7, 8, 9, 10 and an opening e in the optical fibers bundle, The FIG. 4d shows a superior view of the optical fibers geometrical arrangement 7, 8, 9, 10.

The fibers of the bundle, in the figures above mentioned, are configured in a geometrical curved and lengthened form, producing a piece 9 that is likened to a pipe, where in the outlet end 7, or superior, the fibers are positioned side by side, forming a fine and circular line, while in another extremity of the piece 10, or inferior, the fibers are accumulated on an intense light source. The optical fibers arrangement has an optimized geometry to capture the maximum of light in its entry end 10 and conformed to produce a light ring in its outlet 7, by placing of the fibers side by side, in a circular line with diameter of 7 millimeters and with a line width from 50 to 200 microns, since they are formed by fibers of this diameter.

The FIG. 5a, shows the frontal view of the outlet end, of the optical fibers arrangement, with an opening e of optical fibers bundle, details of the endings of the fibers bundles, in that the outlet end of the bundle with the fibers aligned side by side form a ring.

The FIG. 5b, shows a frontal view of the entry end, in that the bundle end entry with the fibers is accumulated around a point.

The FIG. 6 shows a lateral crossed view of the system integrated and mounted on its compartment.

The system has a fixed base of sustenance from which it is possible to adjust the body of the system with the projection and capturing means. These means are mounted in a sliding base in the body of the system, in the horizontal plan when in images acquisition operation.

The system can be configured in four operational ways that carry out four types different of opthalmologic examinations, increasing its applicability. The selection of the spectral band of work is effectuated by a specific combination of optical filters in accordance with the type of examination to be carried out. The optical means of lighting and capturing were optimized to correct aberrations, mainly the chromatic aberration in the band between the blue and the infrared, between 400 and 950 nanometers, due to four types of examinations that will be effectuated. Which are: examination with normal colorful image, also called colorful retinography or "color", where light polarizers are used and a combination of optical filters which allow lighting and capturing in the whole range of the visible; examination with absence of red light, called aneritry retinography or "red free", also with the use of light polarizers and combination of optical filters which promote lighting with green light and capturing in the whole range of the visible; examination called fluorescein angiography, in that is used the property of fluorescence of this substance, which injected in the blood current makes possible an accented contrast of the image obtained in examination of the superficial blood vessels fundus, when filters are used for projection of blue light and capturing of light in the green-yellow band; and examination in the infrared band, so-called indocianine green (ICG), where the property of fluorescence is used in the infrared band of this substance, which injected in the blood current makes possible a contrast accented in examination of the deep blood vessel fundus, when filters are used for projection and capturing of infrared light, respectively in different bands of wavelength, in that this examination allows a deep examination of the choroids since the retina is semitransparent to the infrared.

The Program that controls the acquisition and processing of images, besides displaying results obtained from the images, also was developed for the scheme of operational compatible mode with the configurations described above. This program (software) allows, from each digital image produced and its processing, obtain points to outline the profile of anomalies present in the retina and in the structures of the wall fundus, resulting in the determination of its form and dimension, including dimensional measures for diagnosis. The equipment handling has total operational comfort because it is portable and suitable to be placed where it will be more convenient for the execution of the work. The appropriate adjust to the patient eye is carried out through a gauntlet.

The invention claimed is:

1. A system for obtaining a fundus image, comprising optical means implemented in an equipment to observe and photograph the image of the wall fundus, the optical means comprising:
   a capturing optical means comprising a digital camera to register a captured image by an afocal optical system, the afocal optical system comprising a capturing lens and its afocal complement;
   a lighting optical means comprising an arrangement of optical fiber bundles, and a light source;
   wherein said light beam from the light source has an annular form when it passes in the anterior part of an eyeball and focuses in the pupil plane;
   both means having a partially common optical path over the optical axle from the optical fibers arrangement to the fundus region, such that both beams are coaxial; and
   both optical means equipped with light polarizers integrated with mechanical, electronic and computerized components, and one or more programs.

2. The system for obtaining a fundus image, according to claim 1, wherein the light source is focused by a collimator in the inlet end of a optical fiber intermediary bundle to be focused by a set of condenser lens from the outlet end of the optical fibers intermediary bundle passing through an optical filter to the inlet end of the optical fibers arrangement, which drives and emits a light beam in a ring form in its outlet end, the light beam being projected in the fundus through the capturing lens.

3. The system for obtaining a fundus image, according to claim 1, wherein the capturing optical means and the optical elements of the eye itself form the equivalent of an inverted afocal telescope, and capture the fundus image to form a primary real image in a position between the capturing lens set and its afocal complement, and before the central hole position in the optical fibers arrangement, producing an afocal beam to be registered by the digital camera, with longitudinal mechanical adjust to compensate for patient eye diopter variation, after the beam passes the light polarizer and an optical filter.

4. The system for obtaining a fundus image, according to claim 1, the lighting means further comprising a geometrical arrangement of optical fiber bundles, the geometrical arrangement shaped in a ring in its outlet end, and forming a circle in its inlet end, such that the arrangement has a curved pipe-like profile, and a coaxial hole to the emitting ring in the outlet arrangement and to the optical axle of the system, used as a capturing bundle passage.

5. The system for obtaining a fundus image, according to claim 1, wherein the orientation of a first polarizer element of the lighting optical means has orthogonal orientation to a second polarizer element, and wherein the first polarizer element linearly polarizes the light beam emitted with random polarization in the outlet end of the optical fibers arrangement, and the second polarizer element filters the light with polarization component perpendicular to the orientation obtained by the first polarizer element.

6. The system for obtaining a fundus image, according to claim 1, wherein the capturing lens conjugates the object distance of arrangement outlet end of optical fibers and the image distance of pupillary opening, with respect to the lighting means, and captures an image of fundus forming a primary real image in a position between the capturing lens itself and the central hole of arrangement of optical fibers, with respect to the capturing means.

7. The system for obtaining a fundus image, according to claim 1, and further configured to receive four operational modes, and thereby carry out four types of different ophthalmologic examination, having in the lighting means a light source with wide spectral band, covering infrared light and visible bands, and having in the optical path of both means interchangeable light filters, which may be combined to allow a user to carry out four types of examination with the same equipment, the examination selected from the group consisting of colorful retinography, aneritry retinography, fluorescein angiography and indocianine green.

8. The system for obtaining a fundus image, according to claim 1, further comprising a mechanical adjust for longitudinal movement of lenses forming a focal lens of the capturing camera, that enable optimization of the image focus of fundus on an image sensor, and compensate for diopter variation of the system.

* * * * *